(12) United States Patent
Ibuki et al.

(10) Patent No.: US 6,673,808 B1
(45) Date of Patent: Jan. 6, 2004

(54) MEDICINAL COMPOSITIONS

(75) Inventors: Rinta Ibuki, Kyoto (JP); Fumio Shimojo, Kawanishi (JP); Satoshi Ueda, Kawanishi (JP); Toshihiko Toyoda, Kawanishi (JP); Masayuki Yamanaka, Amagasaki (JP); Erika Yoshida, Kobe (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/673,260

(22) PCT Filed: Apr. 26, 1999

(86) PCT No.: PCT/JP99/02237

§ 371 (c)(1),
(2), (4) Date: Nov. 22, 2000

(87) PCT Pub. No.: WO99/55332

PCT Pub. Date: Nov. 4, 1999

(30) Foreign Application Priority Data

Apr. 27, 1998 (JP) ............................................. 10-117271

(51) Int. Cl.$^7$ ................................................ A61K 31/44
(52) U.S. Cl. ....................................................... 514/291
(58) Field of Search ................................... 514/291, 294

(56) References Cited

U.S. PATENT DOCUMENTS

| | | | | |
|---|---|---|---|---|
| 4,996,193 A | * | 2/1991 | Hewitt et al. | 514/11 |
| 5,385,907 A | * | 1/1995 | Asakura et al. | 514/291 |
| 5,540,931 A | * | 7/1996 | Hewitt et al. | 424/434 |
| 5,939,427 A | * | 8/1999 | Kagayama et al. | 514/291 |

FOREIGN PATENT DOCUMENTS

| | | | |
|---|---|---|---|
| EP | 0812588 | | 12/1997 |
| WO | WO-9613249 | * | 5/1996 |
| WO | WO98/10747 | | 3/1998 |

* cited by examiner

*Primary Examiner*—Zohreh Fay
*Assistant Examiner*—Brian-yong Kwon
(74) *Attorney, Agent, or Firm*—Oblon, Spivak, McClelland, Maier & Neustadt, P.C.

(57) ABSTRACT

To provide a pharmaceutical composition comprising a macrolide compound, such as tricyclic compound (I) or its pharmaceutically acceptable salt, a dissolution/absorption promoter, a pharmaceutical base, and optionally a compatibilizing agent and/or a thickener. It is satisfactory in stability and absorption kinetics and/or a low irritation potential.

6 Claims, No Drawings

MEDICINAL COMPOSITIONS

This application is a 371 of PCT/JP99/02237 filed on Apr. 26, 1999, which application claims priority from JP 10/117271 filed on Apr. 27, 1998.

1. Technical Field

This invention relates to a pharmaceutical composition containing macrolide compound, said composition being stable and having very satisfactory absorption kinetics and/or a low irritation potential. This composition finds application in the therapy and prophylaxis of various diseases of the skin.

2. Background Art

The tricyclic compound and its pharmaceutically acceptable salt, which is a representative of the macrolide compound for use in accordance with this invention, is known to have excellent immunosuppressive activity, antimicrobial activity and other pharmacological activities and, as such, be of value for the treatment or prevention of rejection reactions by transplantation of organs or tissues, graft-vs.-host diseases, autoimmune diseases, and infectious diseases [EP-A-0184162, EP-A-0323042, etc.].

Particularly, FK506 Substance among such tricyclic compound (I), which has been shown to be useful for the therapy and prevention of graft rejection in organ transplantation due to its quite excellent immunosuppressive activity.

It is mentioned in EP-A-0315978 that an ethanol solution of FK506 Substance is effective in arresting inflammatory reactions and that FK506 Substance can be provided in the form of a lotion, a gel or a cream. However, there is no specific disclosure of such dosage forms.

Meanwhile, EP-A-0474126 discloses an ointment comprising FK506 substance and its analogs, a dissolution/absorption promoter added in a sufficient amount to dissolve the active compound, and an ointment base.

Further, WO94/28894 discloses a lotion comprising FK506 substance and its analogs, a dissolution/absorption promoter, a liquid base, and, optionally, an emulsifier and/or a thickener.

In the treatment of diseases of the skin, an ointment transitionally constitutes the cardinal regimen. However, a variety of dosage forms are needed, as a matter of fact, in order to cope with different symptoms or lesions in different sites.

DISCLOSURE OF INVENTION

The inventors of this invention explored in earnest for a pharmaceutical composition suited for the administration of a macrolide compound, a representative of which is FK506 Substance, and discovered a dosage form having very satisfactory characteristics, namely stability, good percutaneous absorption and/or low skin irritation potential. Thus, the present invention specifically relates to a gel preparation comprising the macrolide compound for external application.

In accordance with this invention there is provided a pharmaceutical composition comprising said macrolide compound, a dissolution/absorption promoter and a pharmaceutical base, and optionally a compatibilizing agent and/or a thickener.

The term "macrolide compound" for use in accordance with the invention is the generic name of compounds with 12 members or more, which belong to macrocyclic lactones. Abundant macrolide compounds generated by microorganisms of the genus Streptomyces, such as rapamycin, tacrolimus (FK506), and ascomycin, and the analogs and derivatives thereof are included in the term macrolide compound.

As a particular example of the macrolide compound, the tricyclic compound of the following formula (I) can be exemplified.

(I)

(wherein each of adjacent pairs of $R^1$ and $R^2$, $R^3$ and $R^4$, and $R^5$ and $R^6$ independently
  (a) is two adjacent hydrogen atoms, but $R^2$ may also be an alkyl group or
  (b) may form another bond formed between the carbon atoms to which they are attached;

$R^7$ is a hydrogen atom, a hydroxy group, a protected hydroxy group, or an alkoxy group, or an oxo group together with $R^1$;

$R^8$ and $R^9$ are independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group, (a hydrogen atom and a hydroxy group), (a hydrogen atom and a hydrogen atom), or a group represented by the formula —CH$_2$O—;

Y is an oxo group, (a hydrogen atom and a hydroxy group), (a hydrogen atom and a hydrogen atom), or a group represented by the formula N—NR$^{11}$R$^{12}$ or N—OR$^{13}$;

$R^{11}$ and $R^{12}$ are independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ are independently a hydrogen atom or an alkyl group;

$R^{24}$ is an optionally substituted ring system which may contain one or more heteroatoms;

n is an integer of 1 or 2; and in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkoxy, a benzyl, a group of the formula —CH$_2$Se(C$_6$H$_5$), and an alkyl substituted by one or more hydroxy groups.

Preferable $R^{24}$ may be cyclo(C$_{5-7}$)alkyl group, and the following ones can be exemplified.

(a) a 3,4-di-oxo-cyclohexyl group;
(b) a 3-$R^{20}$-4-$R^{21}$-cyclohexyl group,
   in which $R^{20}$ is hydroxy, an alkoxy group, an oxo group, or a —$OCH_2OCH_2CH_2OCH_3$ group, and
   $R^{21}$ is hydroxy, —OCN, an alkoxy group, a heteroaryloxy which may be substituted by suitable substituents, a —$OCH_2OCH_2CH_2OCH_3$ group, a protected hydroxy group, chloro, bromo, iodo, aminooxalyloxy, an azido group, p-tolyloxythiocarbonyloxy, or $R^{25}R^{26}$CHCOO—,
   in which $R^{25}$ is optionally protected hydroxy or protected amino, and $R^{26}$ is hydrogen or methyl, or
   $R^{20}$ and $R^{21}$ together form an oxygen atom in an epoxide ring; or
(c) cyclopentyl group substituted by methoxymethyl, optionally protected hydroxymethyl, acyloxymethyl (in which the acyl moiety optionally contains either a dimethylamino group which may be quaternized, or a carboxy group which may be esterified), one or more amino and/or hydroxy groups which may be protected, or aminooxalyloxymethyl. A preferred example is a 2-formyl-cyclopentyl group.

The definitions used in the above general formula (I) and the specific and preferred examples thereof are now explained and set forth in detail.

The term "lower" means, unless otherwise indicated, a group having 1 to 6 carbon atoms.

Preferable examples of the "alkyl groups" and an alkyl moiety of the "alkoxy group" include a straight or branched chain aliphatic hydrocarbon residue, for example, a lower alkyl group such as methyl, ethyl, propyl, isopropyl, butyl, isobutyl, pentyl, neopentyl and hexyl.

Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl.

Preferable examples of the "aryl groups" include phenyl, tolyl, xylyl, cumenyl, mesityl and naphthyl.

Preferable protective groups in the "protected hydroxy groups" and the "protected amino" are 1-(lower alkylthio)-(lower)alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably $C_1$–$C_4$ alkylthiomethyl group, most preferably methylthiomethyl group;
trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldiphenylsilyl, propyldiphenylsilyl, tert-butyldiphenyl-silyl, etc.), more preferably tri($C_1$–$C_4$) alkylsilyl group and $C_1$–$C_4$alkyldiphenylsilyl group, most preferably tert-butyldimethylsilyl group and tert-butyldiphenylsilyl group; and an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.; a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri-(lower)alkylsilyl(lower)alkoxycarbonyl(lower) alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar(lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are $C_1$–$C_4$ alkanoyl group optionally having carboxy, cyclo($C_5$–$C_6$)alkoxy($C_1$–$C_4$)alkanoyl group having two ($C_1$–$C_4$) alkyls at the cycloalkyl moiety, camphorsulfonyl group, carboxy-($C_1$–$C_4$)alkylcarbamoyl group, tri($C_1$–$C_4$) alkylsilyl($C_1$–$C_4$)alkoxycarbonyl($C_1$–$C_4$)-alkylcarbamoyl group, benzoyl group optionally having one or two nitro groups, benzenesulfonyl group having halogen, or phenyl ($C_1$–$C_4$)alkanoyl group having $C_1$–$C_4$ alkoxy and trihalo ($C_1$–$C_4$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "5- or 6-membered nitrogen, sulfur and/or oxygen containing heterocyclic ring" include a pyrrolyl group and a tetrahydrofuryl group.

"A heteroaryl which may be substituted by suitable substituents" moiety of the "heteroaryloxy which may be substituted by suitable substituents" may be the ones exemplified for $R^1$ of the compound of the formula of EP-A-532,088, with preference given to 1-hydroxyethylindol-5-yl, the disclosure of which is incorporated herein by reference.

The ticyclic compounds (I) and its pharmaceutically acceptable salt for use in accordance with this invention are well known to have excellent immunosuppressive activity, antimicrobial activity and other pharmacological activities and, as such, be of value for the treatment or prevention of rejection reactions by transplantation of organs or tissues, graft-vs-host diseases, autoimmune diseases, and infectious diseases [EP-A-0184162, EP-A-0323042, EP-A-423714, EP-A-427680, EP-A-465426, EP-A-480623, EP-A-532088, EP-A-532089, EP-A-569337, EP-A-626385, WO89/05303, WO93/05058, WO96/31514, WO91/13889, WO91/19495, WO93/5059, etc.], the disclosures of which are incorporated herein by reference.

Particularly, the compounds which are designated as FR900506 (=FK506), FR900520 (ascomycin), FR900523, and FR900525 are products produced by microorganisms of the genus Streptomyces, such as *Streptomyces tsukubaensis* No. 9993 [deposited with National Institute of Bioscience and Human Technology Agency of Industrial Science and Technology (formerly Fermentation Research Institute Agency of Industrial Science and Technology), at 1–3, Higashi 1-chome, Tsukuba-shi, Ibaraki, Japan, date of deposit Oct. 5, 1984, accession number FERM BP-927] or *Streptomyces hygroscopicus* subsp. yakushimaensis No. 7238 [deposited with National Institute of Bioscience and Human Technology Agency of Industrial Science and Technology (formerly Fermentation Research Institute Agency of Industrial Science and Technology), at 1–3, Higashi 1-chome, Tsukuba-shi, Ibaraki, Japan, date of deposit Jan. 12, 1985, accession number FERM BP-928] [EP-A-0184162]. The FK506 (general name: tacrolimus) of the following chemical formula, in particular, is a representative compound.

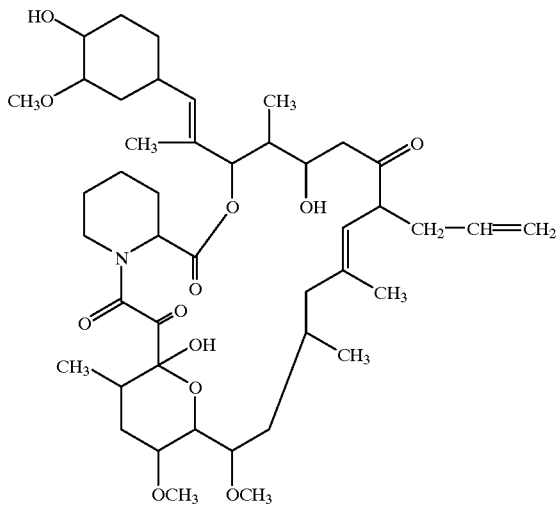

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The preferred examples of the tricyclic compounds (I) are the ones, wherein each of adjacent pairs of $R^3$ and $R^4$ or $R^5$ and $R^6$ independently form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is (a hydrogen atom and a hydrogen atom) or an oxo group;

Y is an oxo group;

each of $R^{14}$, $R^{15}$, $R^{16}$, $R^{17}$, $R^{18}$, $R^{19}$, and $R^{22}$ is a methyl group;

$R^{24}$ is a 3-$R^{20}$-4-$R^{21}$-cyclohexyl group, in which $R^{20}$ is hydroxy, an alkoxy group, an oxo group, or a —OCH$_2$OCH$_2$CH$_2$OCH$_3$ group, and $R^{21}$ is hydroxy, —OCN, an alkoxy group, a heteroaryloxy which may be substituted by suitable substituents, a —OCH$_2$OCH$_2$CH$_2$OCH$_3$ group, a protected hydroxy group, chloro, bromo, iodo, aminooxalyloxy, an azido group, p-tolyloxythiocarbonyloxy, or $R^{25}R^{26}$CHCOO—, in which $R^{25}$ is optionally protected hydroxy or protected amino, and $R^{26}$ is hydrogen or methyl, or $R^{20}$ and $R^{21}$ together form an oxygen atom in an epoxide ring; and n is an integer of 1 or 2.

The most preferable tricyclic compounds (I) is, in addition to FK506, ascomycin derivatives such as halogenated-ascomycin (e.g., 33-epi-chloro-33-desoxyascomycin), which is disclosed in EP 427,680, example 66a.

As the other preferable example of the macrolides as immunosuppressants, rapamycin [THE MERCK INDEX (12th edition), No. 8288] and its derivatives can be exemplified. Preferred example of the derivatives is an O-substituted derivative in which the hydroxy in position 40 of formula A illustrated at page 1 of WO 95/16691, incorporated herein by reference, is replaced by —OR$_1$ in which R$_1$ is hydroxyalkyl, hydroalkoxyalkyl, acylaminoalkyl and aminoalkyl; for example 40-O-(2-hydroxy)ethyl-rapamycin, 40-O-(3-hydroxy)propyl-rapamycin, 40-O-[2-(2-hydroxy)ethoxylethyl-rapamycin and 40-O-(2-acetaminoethyl)-rapamycin. These O-substituted derivatives may be produced by reacting rapamycin (or dihydro or deoxo-rapamycin) with an organic radical attached to a leaving group (for example RX where R is the organic radical which is desired as the O-substituent, such as an alkyl, allyl, or benzyl moiety, and X is a leaving group such as CCl$_3$C(NH)O or CF$_3$SO$_3$) under suitable reaction conditions. The conditions may be acidic or neutral conditions, for example in the presence of an acid like trifluoromethanesulfonic acid, camphorsulfonic acid, p-toluenesulfonic acid or their respective pyridinium or substituted pyridinium salts when X is CCl$_3$C(NH)O or in the presence of a base like pyridine, a substituted pyridine, diisopropylethylamine or pentamethylpiperidine when X is CF$_3$SO$_3$. The most preferable one is 40-O-(2-hydroxy)ethyl rapamycin, which is disclosed in WO94/09010, the disclosure of which is incorporated herein by reference.

The tricyclic compounds(I), and rapamycin and its derivatives, have a similar basic structure, i.e., tricyclic macrolide structure, and at least one of the similar biological properties (for example, immunosupressive activity).

The tricyclic compounds(I), and rapamycin and its derivatives, may be in a form of its salt, which includes conventional non-toxic and pharmaceutically acceptable salt such as the salt with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the macrolide compound used in the present invention, it is to be understood that there may be conformers and one or more stereoisomers such as optical and geometrical isomers due to asymmetric carbon atom(s) or double bond(s), and such conformers and isomers are also included within the scope of macrolide compound in the present invention. And further, the macrolide compounds can be in the form of a solvate, which is included within the scope of the present invention. The solvate preferably include a hydrate and an ethanolate.

The dissolution/absorption promoter for use in this invention is not particularly restricted provided that it is capable of dissolving macrolide compound, such as tricyclic compound (I) or its pharmaceutically acceptable salt, therein and/or promoting its percutaneous absorption. For example, the following monohydric alcohol fatty acid esters, dibasic acid diesters and lower alkylene carbonates can be used with advantage.

Monohydric alcohol fatty acid esters
(isopropyl myristate, ethyl myristate, butyl myristate, isocetyl myristate, octyldodecyl myristate, isopropyl palmitate, isostearyl palmitate, isopropyl isostearate, isocetyl isostearate, butyl stearate, isocetyl stearate, cetyl isooctanotate, ethyl linoleate, isopropyl linoleate, hexyl laurate, ethyl oleate, decyl oleate, oleyl oleate, octyldodecyl myristate, hexyldecyl dimethyloctanoate, octyldodecyl neodecanotate, etc.).

Dibasic acid diesters
(diisopropyl adipate, dimethyl adipate, diethyl adipate, diisopropyl adipate, diethyl sebacate, diisopropyl sebacate, dipropyl sebacate, diethyl phthalate, diethyl pimelate, etc.)

Lower alkylene carbonates
(propylene carbonate, ethylene carbonate, etc.)

In this invention, the dissolution/absorption promoters listed above can be used each independently or in a suitable combination.

Particularly, diethyl sebacate is the most preferable dissolution/absorption promoter in case of considering stability and/or solubility of the active ingredient, and/or smell, color and touch of the composition.

The amount of said dissolution/absorption promoter in the composition is not particularly restricted but should be large enough to dissolve the macrolide compound and/or promote its percutaneous absorption. For example, its amount is preferably 0.1~50% (w/w), more preferably 0.5~30% (w/w), still more preferably 1~20% .(w/w).

The pharmaceutical base for use in this invention is not particularly restricted provided that it is compatible with the other ingredients in the composition and even capable of dissolving the thickener. Particularly, hydrophilic bases capable of dissolving both the macrolide compound and the said thickener are preferred. As such, hydrophilic glycols such as lower alkanediols, e.g. ethylene glycol, propylene glycol, and butylene glycol, are particularly preferred. The amount of the pharmaceutical base in the composition of this invention can be judiciously selected according to its need. Further, it is possible to control the percutaneous absorption of the macrolide compound, by mixing a suitable amount of hydrophilic polymers such as polyethylene glycol with the pharmaceutical base.

The compatibilizing agent for optional use in this invention is a substance which improves the compatibility of the dissolution/absorption promoter with the pharmaceutical base and, as such, includes but is not limited to the following.

Alcohols
(isopropyl alcohol, ethanol, oleyl alcohol, cetanol, stearyl alcohol, 2-octyldodecanol, etc.)

Diethylene glycol mono(lower)alkyl ethers
(diethylene glycol monoethyl ether, diethylene glycol monobutyl ether, etc.)

The most preferred of all are diethylene glycol mono (lower) alkyl ethers, among which diethylene glycol monoethyl ether is particularly preferred. And in case that diethylene glycol monoethyl ether is used, good cutaneous retention of the macrolide compound can be expected. The formulating amount of said compatibilizing agent is not particularly restricted provided that it is added in a sufficient amount to improve the compatibility of the dissolution/absorption promoter with the pharmaceutical base and, as such, may for example be 1~30% (w/w), more preferably 2~20% (w/w), most preferably 5~15% (w/w).

The thickener which is used optionally in this invention is not particularly restricted provided that it is pharmaceutically acceptable and capable of imparting viscosity to the pharmaceutical base, thus including the following organic and inorganic water-soluble macromolecular substances, among others.

(1) Organic substances
Native polymers - - - gum Arabic, gum guar, carrageenan, gum tragacanth, pectin, starch, gum xanthan, gelatin, casein, dextrin, cellulose Semisynthetic polymers - - - cellulose polymer (methylcellulose, ethylcellulose, hydroxyethylcellulose, hydroxypropylcellulose, carboxymethylcellulose sodium, carboxymethylcellulose calcium, etc.), carboxymethylstarch, sodium alginate, propylene glycol alginate Synthetic polymers - - - carboxyvinyl polymer (Carbopol), polyvinyl alcohol, polyvinylpyrrolidone, polyethylene glycol, poly(vinyl methyl ether), sodium polyacrylate (2) Inorganic substances
Bentonite, synthetic magnesium silicate, magnesium aluminosilicate, silicon dioxide, etc.

The pharmaceutical composition of this invention preferably contains a thickener and the amount of the thickener in the pharmaceutical composition can be judiciously selected according to the objective viscosity of the pharmaceutical composition. For example, the thickener is used in a proportion of preferably 0.1~10% (w/w), more preferably 0.5~5%(w/w). Among the specific examples given above, cellulose polymer such as hydroxy-propylcellulose, carboxyvinyl polymer are more preferable, and it is possible to change the touch of the pharmaceutical composition by changing them.

In addition to the above ingredients, the pharmaceutical composition of this invention may contain the conventional excipient (e.g. lactose, sucrose, starch, mannitol, etc.), stabilizer [antioxidant (e.g. ascorbyl palmitate, tocopherol, etc.)], coloring agent, sweetener, perfume, diluent and preservative, as well as other medicinally active substances. Particularly, the stability of the present pharmaceutical composition can be improved if 0.01–1%(w/w), more preferably 0.05–0.1%(w/w) amount of ascorbyl palmitate is used as the stabilizer.

The pharmaceutical composition of this invention can be used by applying it to the affected site, particularly the skin lesion, once to 4 times daily.

The proper amount of said macrolide compounds in the pharmaceutical composition is dependent on its particular species used, the patient's age, the type of disease and its severity, and other factors. Typically, the recommended amount relative to the total composition is 0.001~20% (w/w), more preferably 0.01~10% (w/w), most preferably 0.03~3% (w/w). The composition may further contain one or more other drugs which are indicated in diseases of the skin.

Meanwhile, the pharmaceutical composition of this invention can be produced in the same manner as described in the following examples.

EXAMPLES

The following examples are intended to illustrate this invention in further detail and should by no means be construed as defining the scope of the invention. In the following examples, FK506 is admixed as its monohydrate when preparing compositions containing it, though its amount is expressed as the weight of FK506, not of its monohydrate.

Example 1

[Composition 1]

| | |
|---|---|
| FK506 | 0.3 mg |
| Diethyl sebacate | 10 mg |
| Diethylene glycol monoethyl ether | 10 mg |
| Propylene glycol | q.s. |
| Hydroxypropylcellulose | 2.5 mg |
| Total | 100 mg |

Diethylene glycol monoethyl ether was dissolved in a mixture of propylene glycol and diethyl sebacate and FK506 and hydroxypropylcellulose were then dissolved in the resultant solution, followed by stirring, to provide a gel preparation for external application.

Example 2

According to a similar manner to Example 1, the following pharmaceutical compositions were prepared.

[Composition 2]

| | |
|---|---|
| FK506 | 0.03 mg |
| Diethyl sebacate | 10 mg |
| Diethylene glycol monoethyl ether | 10 mg |
| Propylene glycol | q.s. |
| Total | 100 mg |

[Composition 3]

| | |
|---|---|
| FK506 | 0.03 mg |
| Diethyl sebacate | 10 mg |
| Diethylene glycol monoethyl ether | 10 mg |
| Propylene glycol | q.s. |
| Hydroxypropylcellulose | 2.5 mg |
| Total | 100 mg |

[Composition 4]

| | |
|---|---|
| FK506 | 0.03 mg |
| Diethyl sebacate | 15 mg |
| Diethylene glycol monoethyl ether | 10 mg |
| Propylene glycol | q.s. |
| Hydroxypropylcellulose | 2.5 mg |
| Total | 100 mg |

[Composition 5]

| | |
|---|---|
| Ascomycin | 0.3 mg |
| Diisopropyl adipate | 10 mg |
| Diethylene glycol monoethyl ether | 10 mg |
| Butylene glycol | q.s. |
| Hydroxypropylcellulose | 2.5 mg |
| Total | 100 mg |

[Composition 6]

| | |
|---|---|
| FK506 | 0.3 mg |
| Diethyl sebacate | 10 mg |
| Propylene glycol | q.s. |
| Total | 100 mg |

Composition 7

| | |
|---|---|
| FK506 | 0.3 mg |
| Diethyl sebacate | 10 mg |
| Diethylene glycol monoethyl ether | 10 mg |
| Propylene glycol | q.s. |
| Carbopol | 2.5 mg |
| Total | 100 mg |

[Composition 8]

| | |
|---|---|
| FK506 | 0.3 mg |
| Diethyl sebacate | 10 mg |
| Diethylene glycol monoethyl ether | 10 mg |
| Propylene glycol | 38.59 mg |
| Polyethylene glycol | 38.59 mg |
| Ascorbyl palmitate | 0.02 mg |
| Carbopol | 2.5 mg |
| Total | 100 mg |

Example 3

According to a similar manner to Example 1, the following pharmaceutical compositions 9, 10, 11 were prepared.

| | Composition No. | | |
|---|---|---|---|
| | 9 (% w/w) | 10 (% w/w) | 11 (% w/w) |
| FK506 | 1.00 | 0.30 | 0.10 |
| Diethyl sebacate | 10.00 | 10.00 | 10.00 |
| Diethylene glycol monoethyl ether | 10.00 | 10.00 | 10.00 |
| Propylene glycol | 76.48 | 77.18 | 77.38 |
| Ascorbyl palmitate | 0.02 | 0.02 | 0.02 |
| Hydroxypropylcellulose | 2.5 | 2.5 | 2.5 |

Example 4

According to a similar manner to Example 1, the following pharmaceutical compositions 12, 13, 14 were prepared.

| | Composition No. | | |
|---|---|---|---|
| | 12 (% w/w) | 13 (% w/w) | 14 (% w/w) |
| Ascomycin | 1.00 | — | — |
| 33-epi-chloro-33-desoxy-ascomycin | — | 1.00 | — |
| 40-O-(2-Hydroxy) ethyl-rapamycin | — | — | 1.00 |
| Diethyl sebacate | 10.00 | 10.00 | 10.00 |
| Diethylene glycol monoethyl ether | 10.00 | 10.00 | 10.00 |
| Propylene glycol | 76.48 | 76.48 | 76.48 |
| Ascorbyl palmitate | 0.02 | 0.02 | 0.02 |
| Hydroxypropylcellulose | 2.5 | 2.5 | 2.5 |

Example 5

The percutaneous absorption and cutaneous retention experiments performed using the pharmaceutical composition of the invention are described below.

Using Composition 1 of Example 1, an in vivo percutaneous absorption experiment and a cutaneous retention (residue in skin) experiment were carried out.

As experimental animals, three 7-week-old male SD rats were used. With each animal immobilized in supine position in a stereotaxic device, the hair coat was removed with an electric clipper and a depilatory cream (Eva Cream, manufacture by Tokyo Tanabe Co.) was applied to the clipped area. After application of the cream, the local skin was washed with water for 10 minutes to remove the hairs and the animal was returned to the cage and kept intact for 24 hours. After the animal was immobilized again in supine position in the stereotaxic device, a 2.5 cm×4 cm area was marked off on the depilated abdominal skin of the rat and 50 mg of the test drug was applied to said marked-off area. At predetermined times after medication, 0.3 ml of blood was withdrawn from the subclavian vein into an EDTA-containing syringe and, after through mixing of blood with EDTA, the blood sample was stored frozen until assayed. The whole blood concentration of FK506 Substance was determined by subjecting the blood sample to the enzyme immunoassay using a peroxidase (the assay system described in, for example, Japanese Kokai Tokkyo Koho H1-92659).

On the other hand, after blood sampling at the 24th hour, the surface of the medicated skin was washed with water and the skin tissue was excised from the above-mentioned marked-off area. After the subcutaneous adipose tissue was removed from the isolated skin, the skin tissue was homogenized in 0.1N-HCl/ethanol (1/1) to prepare a 1% (w/w) skin tissue homogenate. The amount of FK506 Substance in this homogenate was determined by the enzyme immunoassay described above.

The percutaneous absorption parameters of the test drug were determined. The results are presented in Table 1. In Table 1, AUC [0~24 hr] denotes the area under the 0~24 hr blood concentration-time curve.

TABLE 1

| Sample administered | AUC [0–24 hr] (ng · hr/ml) | Residue in skin (%) (after 24 hr) |
|---|---|---|
| Composition 1 | >30 | >5 |

Effect of the Invention

In accordance with this invention there was provided a pharmaceutical composition containing the macrolide compound, particularly the tricyclic compound (I) or its pharmaceutically acceptable salt, which is very satisfactory in stability, workability, user acceptance, irritation potential and/or dermal penetration efficiency. In particular, a gel preparation for external application could be provided which insures an improved penetration of the macrolide compound, particularly said tricyclic compound (I) or its pharmaceutically acceptable salt, through the keratoid layer, which is a barrier to absorption, as well as a good cutaneous retention (particularly in the dermis) of the macrolide compound. In addition, the pharmaceutical composition of this invention has an adequate emollient (humectant) action and is free from the risk for dermatrophy and the so-called rebound phenomenon.

The pharmaceutical composition of the present invention is useful for the treatment or prevention of inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysisbullosa, urticaria, angioedema, vasculitides, erythema, dermal eosinophilia, lupus erythematosus, acne, and alopecia areata) because of the pharmacologic activities possessed by the macrolide compound. Particularly, the gel preparatrion for external use of the present invention is useful for the treatment or prophylaxis of psoriasis, such as psoriasis arthropathica, psoriasis circinata, psoriasis diffusa, psoriasis discoidea, generalized pustular psoriasis of Zumbusch, psoriasis geographica, psoriasis guttata, psoriasis gyrata, psoriasis inveterata, psoriasis nummularis, psoriasis orbicularis, psoriasis ostreacea, psoriasis punctata, pustular psoriasis, psoriasis spondylitica, psoriasis universalis, and so on.

Furthermore, the pharmaceutical composition of the present invention is useful for the therapy or prophylaxis of the following diseases.

Autoimmune diseases of the eye (e.g. keratoconjunctivitis, vernal conjunctivitis, uveitis associated with behcet's disease, keratitis, herpetic keratitis, conical keratitis, corneal epithelial dystrophy, keratoleukoma, ocular premphigus, mooren's ulcer, scleritis, graves' ophthalmopathy, Vogt-Koyanagi-Harada syndrome, keratoconjunctivitis sicca (dry eye), phlyctenule, iridocyclitis, sarcoidosis, endocrine ophthalmopathy, etc.);

skin diseases (e.g. dermatomyositis, leukoderma vulgaris, ichthyosis vulgaris, photosensitivity, and cutaneous T-cell lymphoma);

hypertrophic cicatrix or keloid due to trauma, burn, or surgery.

The disclosure of the patents, patent applications and references cited herein in the present application is encompassed within the description of the present specification.

What is claimed is:

1. A pharmaceutical composition, which is consisting essentially of a tricyclic compound, a dissolution/absorption promoter, a pharmaceutical base, a compatibilizing agent and a thickener, wherein said tricyclic compound is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-22.3.1.0$^{4,9}$] octacos-18-ene-2,3,10,16-tetraone or its hydrate; the dissolution/absorption promoter is diethyl sebacate; the pharmaceutical base is a hydrophilic glycol; the compatibilizing agent is diethylene glycol monoethyl ether; and the thickener is cellulose polymer or carboxyvinyl polymer.

2. The pharmaceutical composition according to claim 1, which is in a gel form.

3. The pharmaceutical composition according to claim 1, in which the hydrophilic glycol is a lower alkanediol.

4. The pharmaceutical composition according to claim 3, in which the hydrophilic glycol is propylene glycol.

5. The pharmaceutical composition according to claim 1, in which the amount of the tricyclic compound to the total composition is about 0.03–3 wt % (w/w).

6. The pharmaceutical composition according to claim 1, in which the amount of the dissolution/absorption promoter and the compatibilizing agent to the total composition is about 1–20 wt % (w/w) and about 5–15% (w/w), respectively.

* * * * *